United States Patent [19]
Salek et al.

[11] Patent Number: 5,763,644
[45] Date of Patent: Jun. 9, 1998

US005763644A

[54] METHOD FOR TRANSESTERIFICATION

[75] Inventors: Jeffrey S. Salek; Joseph Pugach, both of Allegheny County, Pa.

[73] Assignee: Aristech Chemical Corporation, Pittsburgh, Pa.

[21] Appl. No.: 630,087

[22] Filed: Apr. 8, 1996

[51] Int. Cl.$^6$ .................................................. C07C 69/63
[52] U.S. Cl. .................................................. 560/217
[58] Field of Search .................................................. 560/217

[56] References Cited

U.S. PATENT DOCUMENTS

| | | | |
|---|---|---|---|
| 3,714,234 | 1/1973 | White | 260/486 R |
| 4,117,238 | 9/1978 | Ackermann et al. | 560/217 |
| 4,228,084 | 10/1980 | Ackermann et al. | 260/348.12 |

FOREIGN PATENT DOCUMENTS

| | | |
|---|---|---|
| 562358 | 8/1958 | Canada. |
| 976304 | 11/1964 | United Kingdom. |

*Primary Examiner*—Paul J. Killos

[57] ABSTRACT

An improved method for transesterification of acrylate and alkyl acrylate esters. The improved method comprises the use of at least one aromatic amine compound having no acidic or ionic groups. The improved inhibitor system enhances the reaction rate of the transesterification reaction while simultaneously maintaining adequate polymerization suppression. The reaction is catalyzed by a basic catalyst, and can be driven by the removal of alcohol as an alcohol/saturated hydrocarbon azeotrope.

5 Claims, No Drawings

METHOD FOR TRANSESTERIFICATION

TECHNICAL FIELD

The present invention relates to an improved method for effecting transesterification reactions of acrylate and alkylacrylate esters. The improved method utilizes an inhibitor system having at least one aromatic amine compound that does not contain ionic or acidic groups. The inhibitor system enhances the reaction rate of the transesterification reaction while maintaining adequate polymerization suppression. The reactions are catalyzed by a basic catalyst and can be driven by the azeotropic removal of alcohol.

BACKGROUND OF THE INVENTION

There are numerous methods available for preparing acrylate and alkylacrylate esters. These methods include direct and transesterification (ester interchange) reactions. One common feature of prior art transesterification processes is the use of aromatic inhibitor compounds such as hydroquinone and 4-methoxyphenol which contain ionic or acidic groups. If the acrylate or alkylacrylate ester synthesis occurs via the transesterification pathway, a base catalyst can be utilized in the presence of polymerization inhibitor(s). For example, British Patent No. 976,304 discloses a process for the preparation of an ester of acrylic or methacrylic acid by transesterification. The reaction utilizes a phenate catalyst in an amount which is at least stoichiometric with respect to the alcohol. The phenate catalyst can be prepared either in situ, or prior to transesterification.

White, in U. S. Pat. No. 3,714,234, discloses catalysts obtained from the reaction product of a tin containing compound and an alkali-metal phenoxide. These catalysts are used in the preparation of methacrylate esters such as 2-ethyl-1-hexylmethacrylate.

As can be seen from prior art processes, amine-type polymerization inhibitors represent a widely utilized group of polymerization inhibiting compounds. These aromatic compounds are exemplified in U.S. Pat. Nos. 4,117,238 and 4,228,084, which illustrate their application to transesterification reactions. However, a significant drawback to the prior art systems is that the inhibitors used have at least one acidic hydrogen, and therefore become ionic under basic conditions. The prior art shows the inhibitor can be used alone, or as is often the case, in combination with inhibitors having no ionic or acidic groups, such as phenothiazine. By non-acidic and non-ionic inhibitors is meant those inhibitors which do not contain an acidic hydrogen. As a result, although polymerization is inhibited with an ionic inhibitor, the base-catalyzed transesterification reaction rate is simultaneously affected. The reaction rate is retarded as compared to the instant process.

The present invention is a novel approach to acrylate and alkylacrylate ester synthesis. This process includes the use of at least one aromatic amine inhibitor having no acidic or ionic groups, in the absence of prior art ionic aromatic compounds. As a result, reaction rates are enhanced while adequate polymerization suppression is achieved.

SUMMARY OF THE INVENTION

This invention is drawn to a novel inhibitor system utilized in the transesterification syntheses of acrylate and alkylacrylic esters. The transesterification reaction can be driven in part by the azeotropic removal of the product alcohol. For instance, if the starting ester is methyl methacrylate (MMA), the product methanol can be removed as a $C_5$–$C_8$ saturated hydrocarbon azeotrope or as a MMA/methanol azeotrope.

The feed ester and alcohol are reacted in the presence of a basic catalyst. Potassium alkoxides and hydroxides have been found to be efficient catalysts due to the ease with which they can be removed from the reaction mixture. The potassium catalyst has the unique feature of allowing the reaction to be effectively run at temperatures lower than prior art processes. This is advantageous because ester monomers of the present invention will have a tendency to polymerize quickly at temperatures above 100° C. The reaction of the present invention should be run at temperatures at or below 100° C. Additionally, the need for acidic and ionic polymerization inhibitors is obviated. The present invention can be performed at 1 to 5:1 ester to starting alcohol equivalents. Typically, the ratio will be about 1.1 to 3.0:1.

The basic catalyst is typically added incrementally, and is used in combination with the improved inhibitor system of the present invention. As stated above, the ester materials of the transesterification reaction are prone to rapid polymerization at moderately high temperatures and also at extended reaction times. Even at temperatures below 100° C., the monomers will tend to polymerize under the transesterification reaction conditions. Therefore, it is advantageous to perform the transesterification using an effective polymerization inhibitor system, as well as to minimize the time of reaction.

The present invention is an inhibitor system containing at least one aromatic amine compound having no acidic or ionic groups. The use of such an inhibitor is a departure from prior art transesterification processes, wherein compounds having acidic and ionic groups are used as catalysts and/or inhibitors. In the present invention, the use of a neutral, non-ionic inhibitor system unexpectedly enhances the rate of reaction while maintaining adequate polymerization suppression.

DETAILED DESCRIPTION OF THE INVENTION

An acrylic or alkylacrylic ester is reacted with an alcohol in the presence of a basic catalyst and the present invention inhibitor. The ester is preferably an alkylmethacrylate and the alcohol is preferably a polyol. The reaction product preferably is an alkoxylated bisphenol-A dimethacrylate or ethylene glycol dimethacrylate, and an alcohol. Most preferably, the reacted compounds are methyl methacrylate, and ethoxylated bisphenol-A or ethylene glycol. The product alcohol may be removed as one of the aforementioned azeotropes.

The basic catalyst of the present invention is a potassium alkoxide or hydroxide. Preferably, the catalyst is selected from the group consisting of potassium hydroxide, potassium methoxide, potassium ethoxide, potassium propoxide, and potassium butoxide and the like. The catalyst is typically added incrementally until a total of about 0.04 to about 4.0% by weight of the reaction mixture is delivered. Preferably, about 0.2 to about 1.0% is used.

The inhibitor system is employed in the absence of aromatic inhibitor(s) having acidic and/or ionic groups. Most preferably, the inhibitor system comprises phenothiazine. However, other aromatic inhibitors having no acidic and ionic groups may be used. Other compounds may be present in the present inhibitor system provided these compounds do not offset the synergestics of the system.

The inhibitor compound is added either initially or incrementally until a total of about 0.01 to about 2.0% by weight of the starting alcohol is added. Preferably, 0.1 to 1.0% is used.

The above reaction is preferably run at as low a temperature as possible. Usually within the range of about 65 to about 100° C. More preferably at about 70 to about 90° C., and most preferably 75 to 80° C. The reaction may be run under vacuum, but is preferably performed at atmospheric pressure.

The invention is illustrated by, but not limited to the following examples. Table I presents the results in comparative format.

EXAMPLE 1

Into an apparatus consisting of a four-neck, one liter roundbottom flask equipped with a thermowell, agitator, addition funnel/anhydrous air bleed, and a reflux-controlled ten-tray Oldershaw distillation column/cold-water condenser (<10° C.), was added the following materials: 62.1 g ethylene glycol (1.00 mol), 400.5 g methyl methacrylate (4.00 mol), 0.14 g phenothiazine (700 mmol), and 0.10 g potassium methoxide (1400 mmol). The reaction mixture was heated to a moderate boil at atmospheric pressure. The temperature of the reaction mixture was maintained at 75° C. by adding hexanes as needed. After column equilibration was achieved (the column was considered to be equilibrated once the temperature at Oldershaw column tray #5 decreased to its lowest point), distillate was removed at a 3:1 reflux ratio until the temperature on the Oldershaw column tray #5 increased 15° C. above its lowest temperature. The reaction mixture was then cooled to 50° C. and another increment of 0.10 g potassium methoxide catalyst was added. Heating was reinitiated and distillate was collected as before. Repeating the process through three more incremental potassium methoxide additions (another 0.14 g increment of phenothiazine was added and the reflux ratio was adjusted to 8:1 after the fifth potassium methoxide addition, and the reaction was terminated when the vapor take-off temperature increased 15° C. above its lowest temperature) gave a reaction conversion of 98% (as determined by methanol collection) in 2.6 hours (the total reaction time represents the time of distillate collection). Polymer formation was not detected. (The test for polymer formation involved mixing 3 drops of the reaction mixture effluent with approximately 3 g of methanol. Cloudiness or precipitate formation is indicative of polymer formation.)

EXAMPLE 2

The reagents were blended and the reaction was run as described in Example 1 except that 0.14 g 4-methoxyphenol (1100 mmol) was added in the initial charge and another 0.14 g after the fifth potassium methoxide addition. After 2.3 hours, an 85% conversion was obtained. As can be seen from Table I, polymer formation was not detected. However, the addition of the methoxyphenol inhibitor significantly compromised the reaction rate.

EXAMPLE 3

The reagents were blended and the reaction was run as described in Example 2 except that 0.14 g hydroquinone (1300 mmol) was substituted for 4-methoxyphenol initially and another 0.14 g after the fifth potassium methoxide addition. After performing the reaction through the second potassium methoxide addition, the reaction was terminated due to exceedingly long equilibration times. After 0.4 hours, the conversion obtained was 10%. Polymer formation was not detected.

EXAMPLE 4

Into an apparatus consisting of a four-neck, one liter roundbottom flask equipped with a thermowell, agitator, addition funnel/anhydrous air bleed, and a reflux-controlled ten-tray Oldershaw distillation column/cold-water condenser (<10° C.), was added the following materials: 246 g 6-ethoxylated BPA (0.500 mol), 163 g methyl methacrylate (1.63 mol), 0.27 g phenothiazine (1400 mmol), and 0.15 g potassium methoxide (2100 mmol). After column equilibration was achieved (the column was considered to be equilibrated once the temperature at Oldershaw column tray #5 decreased to its lowest point), distillate was removed at a 8:1 reflux ratio until the temperature on the Oldershaw column tray #5 increased 15° C. above its lowest temperature. The reaction mixture was then cooled to 50° C. and another increment of 0.15 g potassium methoxide catalyst was added. Heating was reinitiated and distillate was collected as before. Repeating the process through two more incremental potassium methoxide additions (another 0.14 g increment of phenothiazine was added after the fourth potassium methoxide addition, and the reaction was terminated when the vapor take-off temperature increased 15° C. above its lowest temperature) gave a reaction conversion of 100% (as determined by methanol collection) in 3.6 hours (the total reaction time represents the time of distillate collection). Polymer formation was minimal. (The test for polymer formation involved mixing 3 drops of the reaction mixture effluent with approximately 3 g of methanol. Cloudiness or precipitate formation is indicative of polymer formation.)

EXAMPLE 5

The reagents were blended and the reaction was run as described in Example 4 except that 0.27 g 4-methoxyphenol (2200 mmol) was added in the initial charge and another 0.27 g following the fourth potassium methoxide addition. After 3.4 hours, a 95% conversion was obtained. Polymer formation was evident. (The test for polymer formation involved mixing 3 drops of the reaction mixture effluent with approximately 3 g of methanol. Cloudiness or precipitate formation was indicative of polymer formation.) Here, the addition of the methoxyphenol inhibitor affected the reaction rate significantly.

TABLE I

| Example | One | Two | Three | Four | Five |
| --- | --- | --- | --- | --- | --- |
| Ester | EGDM | EGDM | EGDM | 6-EBAD | 6-EBAD |
| Inhibitor | PTZ | MP/PTZ | HQ/PTZ | PTZ | MP/PTZ |
| Conversion | 98% | 85% | 10% | 100% | 95% |
| Time (hours) | 2.6 | 2.3 | 0.4 | 3.6 | 3.4 |
| Polymer Test | neg. | neg. | neg. | minimal | pos. |

PTZ = phenothiazine
MP = 4-methoxyphenol
HQ = hydroquinone
EGDM = ethylene glycol dimethacrylate
6-EBAD = 6-ethoxylated bisphenol-A dimethacrylate

We claim:

1. A method of making an alkoxylated bisphenol-A diacrylate or dimethacrylate comprising the steps of:

(a) reacting under transesterification conditions, an acrylic or alkylacrylic ester and an alkoxylated bisphenol-A in the presence of a basic catalyst and at least one polymerization inhibitor consisting essentially of an aromatic amine compound, said aromatic amine compound having no acidic and ionic groups, and wherein said alkoxylated bisphenol-A diacrylate or dimethacrylate is formed; and (b) recovering said alkoxylated bisphenol-A diacrylate or dimethacrylate.

2. A method according to claim 1 wherein said alkoxylated bisphenol-A is ethoxylated bisphenol-A.

3. A method according to claim 1 wherein said acrylic or alkylacrylic ester is methyl methacrylate.

4. A method according to claim 1 wherein said basic catalyst is selected from the group consisting of potassium alkoxides and hydroxide.

5. A method according to claim 1 wherein said at least one inhibitor is phenothiazine.

* * * * *